US008659242B2

(12) United States Patent
Yabe

(10) Patent No.: US 8,659,242 B2
(45) Date of Patent: Feb. 25, 2014

(54) LIGHT SOURCE APPARATUS

(71) Applicant: Olympus Medical Systems Corp., Tokyo (JP)

(72) Inventor: Yusuke Yabe, Chofu (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/685,240

(22) Filed: Nov. 26, 2012

(65) Prior Publication Data

US 2013/0154509 A1    Jun. 20, 2013

Related U.S. Application Data

(63) Continuation of application No. PCT/JP2012/062382, filed on May 15, 2012.

(30) Foreign Application Priority Data

May 26, 2011    (JP) .................................. 2011-118198

(51) Int. Cl.
H05B 37/02    (2006.01)
H01J 13/32    (2006.01)

(52) U.S. Cl.
USPC ........................................ 315/360; 315/112

(58) Field of Classification Search
USPC ........... 315/291, 307, 308, 312, 246, 224, 32, 315/112, 117, 360; 345/204, 206, 690, 691
See application file for complete search history.

(56) References Cited

U.S. PATENT DOCUMENTS

| 2006/0028155 A1* | 2/2006 | Young ........................... 315/308 |
| 2011/0085576 A1* | 4/2011 | Crawford et al. .......... 372/38.07 |
| 2011/0109243 A1* | 5/2011 | Kim et al. ..................... 315/294 |
| 2011/0115409 A1* | 5/2011 | Schwartz et al. ............. 315/297 |

FOREIGN PATENT DOCUMENTS

| JP | 2000-029980 A | 1/2000 |
| JP | 2006-067690 A | 3/2006 |
| JP | 2007-028741 A | 2/2007 |
| JP | 2010-166498 A | 7/2010 |

* cited by examiner

*Primary Examiner* — Minh D A
(74) *Attorney, Agent, or Firm* — Scully, Scott, Murphy & Presser, P.C.

(57) ABSTRACT

A light source apparatus has a lighting time period measuring section measuring lighting time periods of respective LEDs, a junction temperature calculating section that calculates junction temperatures of the respective LEDs, a light intensity deterioration characteristic storing section storing light intensity deterioration characteristics based on the junction temperatures of the respective LEDs, a light source drive characteristic storing section storing characteristics of power that drives the respective LEDs and light intensities, a deteriorated light intensity calculating section calculating deteriorated light intensities based on the measured lighting time periods, the calculated junction temperatures, and the light intensity deterioration characteristics stored in the light intensity deterioration characteristic storing section, and a light source power control section controlling power that drives the light sources, based on the deteriorated light intensities calculated by the deteriorated light intensity calculating section, and the characteristics stored in the light source drive characteristic storing section.

2 Claims, 6 Drawing Sheets

FIG.2

| RELATIVE ADDRESS | CONTENTS |
|---|---|
| 0 | WHITE COLOR LED LIGHTING TIME PERIOD (JUNCTION TEMPERATURE 80 - 90 °C) |
| 4 | WHITE COLOR LED LIGHTING TIME PERIOD (JUNCTION TEMPERATURE 90 - 100 °C) |
| 8 | WHITE COLOR LED LIGHTING TIME PERIOD (JUNCTION TEMPERATURE 100 - 110 °C) |
| C | WHITE COLOR LED LIGHTING TIME PERIOD (JUNCTION TEMPERATURE 110 - 120 °C) |
| 10 | WHITE COLOR LED LIGHTING TIME PERIOD (JUNCTION TEMPERATURE 120 - 130 °C) |
| 14 | WHITE COLOR LED LIGHTING TIME PERIOD (JUNCTION TEMPERATURE 130 - 140 °C) |
| 18 | WHITE COLOR LED LIGHTING TIME PERIOD (JUNCTION TEMPERATURE 140 - 150 °C) |
| 1C | PURPLE LED LIGHTING TIME PERIOD (JUNCTION TEMPERATURE 80 - 90 °C) |
| 20 | PURPLE LED LIGHTING TIME PERIOD (JUNCTION TEMPERATURE 90 - 100 °C) |
| 24 | PURPLE LED LIGHTING TIME PERIOD (JUNCTION TEMPERATURE 100 - 110 °C) |
| ⋮ | ⋮ |

FIG.3

| JUNCTION TEMPERATURE [°C] | WHITE COLOR LED DETERIORATION FACTOR [% / TIME PERIOD] | PURPLE LED DETERIORATION FACTOR [% / TIME PERIOD] |
|---|---|---|
| 80 - 90 | 0.00200 | 0.00133 |
| 90 - 100 | 0.00300 | 0.00167 |
| 100 - 110 | 0.00417 | 0.00250 |
| 110 - 120 | 0.00550 | 0.00333 |
| ⋮ | ⋮ | ⋮ |

FIG.4

| JUNCTION TEMPERATURE [°C] | WHITE COLOR LED USE TIME PERIOD | PURPLE LED USE TIME PERIOD | WHITE COLOR LED DETERIORATION RATE [%] | PURPLE LED DETERIORATION RATE [%] |
|---|---|---|---|---|
| 80 - 90 | 0 | 0 | 0.00 | 0.00 |
| 90 - 100 | 500 | 200 | 1.50 | 0.33 |
| 100 - 110 | 2000 | 500 | 8.34 | 1.25 |
| 110 - 120 | 500 | 300 | 2.75 | 1.00 |
| Total | 3000 | 1000 | 12.59 | 2.58 |

LIGHT SOURCE APPARATUS

CROSS REFERENCE TO RELATED APPLICATION

This application is a continuation application of PCT/JP2012/062382 filed on May 15, 2012 and claims benefit of Japanese Application No. 2011-118198 filed in Japan on May 26, 2011, the entire contents of which are incorporated herein by this reference.

BACKGROUND OF THE INVENTION

1. Field of the Invention

The present invention relates to a light source apparatus, and more particularly to a light source apparatus that calculates a junction temperature, and controls electric power that drives a light source.

2. Description of the Related Art

Conventionally, a light source apparatus has been developed which is capable of special light imaging such as narrow band observation (narrow band imaging: NBI) that enables observation of a vicinity of a mucosal epithelium of living tissue, in addition to normal observation (white light imaging: WLI) using white color illumination. In the light source apparatus, a turret including a plurality of optical filters is included, and an optical filter corresponding to an imaging mode is disposed on an optical path of a xenon lamp, whereby switching of a mode of normal observation or special light imaging is realized.

Further, in recent years, with enhancement in the light intensity of a white color LED, light source apparatuses using LEDs have also been developed in an endoscope field. Further, in the endoscope field, needs for narrow band observation are growing, and therefore, a configuration of a light source apparatus that can perform narrow band observation by using a white color LED and a purple LED is contrived.

FIG. 8 is a diagram showing light intensity deterioration characteristics of a white color LED and a purple LED. As shown in FIG. 8, the white color LED and the purple LED have different light intensity deterioration characteristics, and therefore even with the same lighting time periods, the light intensities of the white color LED and the purple LED differ from each other. Therefore, the light source apparatus including LEDs of a plurality of colors needs processing of correcting the light intensity of each of the respective LEDs.

For example, Japanese Patent Application Laid-Open Publication No. 2000-29980 discloses the optical reading apparatus that can extend the product life by automatically compensating deterioration of the LEDs due to secular change, and can keep a sufficient reading ability for a long period of time. The optical reading apparatus executes deterioration compensation processing after 3000 hours and 5000 hours by estimating reduction, namely, deterioration of luminance of the LEDs due to secular change.

SUMMARY OF THE INVENTION

A light source apparatus of one aspect of the present invention is a light source apparatus configured by a light source having a semiconductor device, a light intensity of which deteriorates with a lighting time period, and includes a lighting time period measuring section that measures a lighting time period of the light source, a junction temperature calculating section that calculates a junction temperature of the light source, a light intensity deterioration characteristic storing section that stores a light intensity deterioration characteristic based on the junction temperature of the light source, a light source drive characteristic storing section that stores characteristics of power that drives the light source and a light intensity, a deteriorated light intensity calculating section that calculates a deteriorated light intensity based on the lighting time period measured by the lighting time period measuring section, the junction temperature calculated by the junction temperature calculating section, and the light intensity deterioration characteristic stored in the light intensity deterioration characteristic storing section, and a light source power control section that controls power that drives the light source, based on the deteriorated light intensity calculated by the deteriorated light intensity calculating section, and the characteristics stored in the light source drive characteristic storing section.

BRIEF DESCRIPTION OF THE DRAWINGS

FIG. 2 is a diagram for explaining an example of an address map of a memory that stores a lighting time period of each of respective LEDs of each junction temperature range;

FIG. 3 is a diagram for explaining an example of a deterioration factor table;

FIG. 4 is a diagram for explaining a calculation example of a deterioration rate;

DETAILED DESCRIPTION OF THE PREFERRED EMBODIMENT

Hereinafter, an embodiment of the present invention will be described in detail with reference to the drawings.

First, based on FIG. 1, a configuration of an endoscope system having a light source apparatus according to one embodiment of the present invention will be described.

Figure 1:
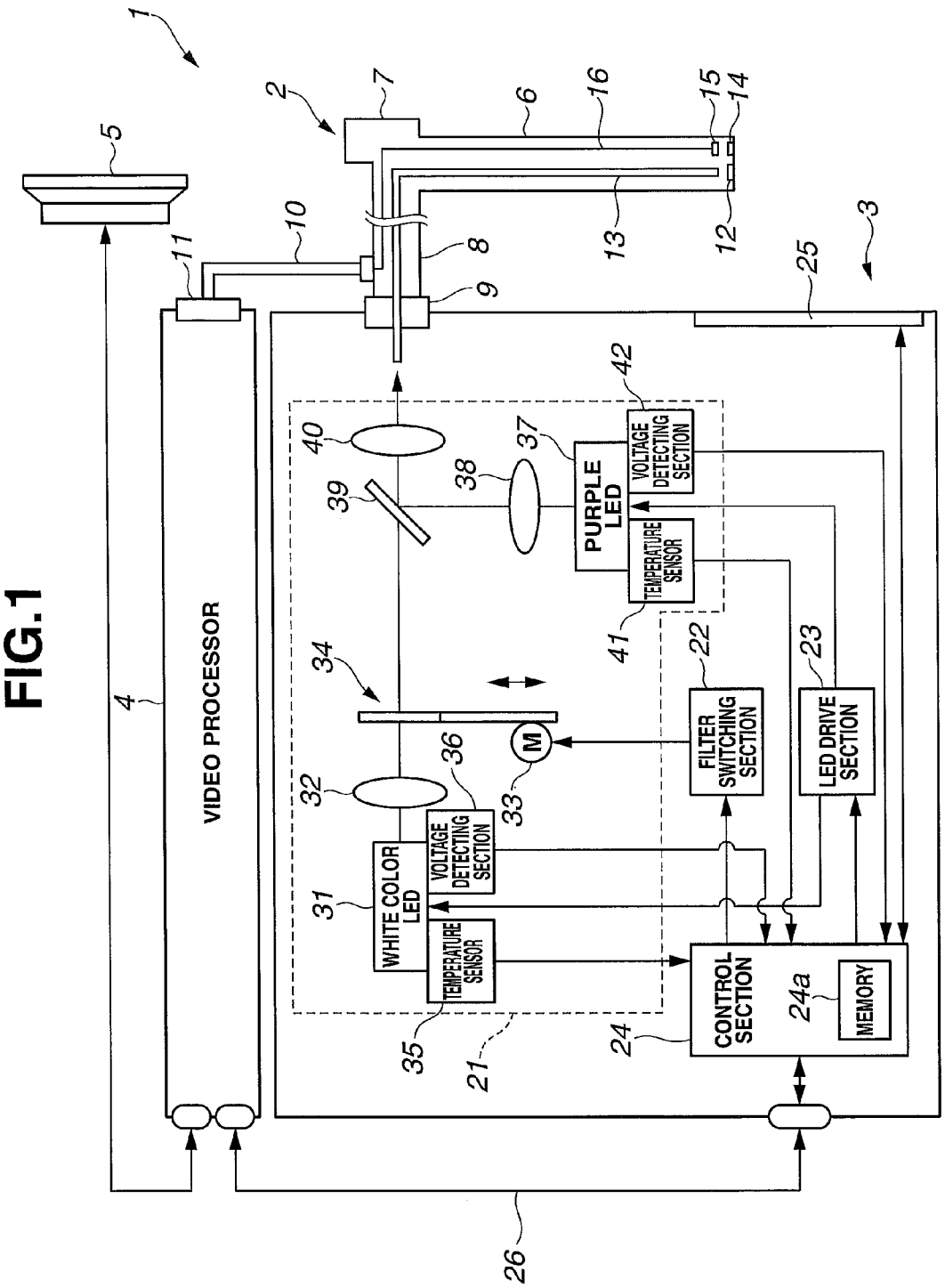
FIG. 1 is a diagram showing a configuration of an endoscope system having a light source apparatus according to one embodiment of the present invention.

FIG. 1 is a diagram showing the configuration of the endoscope system having the light source apparatus according to one embodiment of the present invention.

As shown in FIG. 1, an endoscope system 1 is configured by having an endoscope 2 that picks up an image of an object of an inside of a living body and outputs an image pickup signal, a light source apparatus 3 that supplies an illuminating light for illuminating the object to the endoscope 2, a video processor 4 that converts the image pickup signal outputted from the endoscope 2 into a video signal and outputs the video signal, and a monitor 5 that displays an image corresponding to the video signal outputted from the video processor 4.

The endoscope 2 is configured by having an elongated insertion portion 6 that can be inserted into an inside of a living body, an operation section 7 that is formed at a rear end of the insertion portion 6, a universal cable 8 extended from the operation section 7, a light source connector 9 provided at an end portion of the universal cable 8, an electric cable 10 extended from a side portion of the light source connector 9, and an electric connector 11 provided at an end portion of the electric cable 10. The endoscope 2 is configured to be detachable with respect to the light source apparatus 3 by the light source connector 9 that is provided at the end portion of the universal cable 8, and is configured to be detachable with respect to the video processor 4 by the electric connector 11 that is provided at the end portion of the electric cable 10.

An illumination lens 12 that illuminates an observation target is provided at a distal end portion of the insertion portion 6. A distal end portion of a light guide 13 that guides an illuminating light is provided at a rear end face of the illumination lens 12. The light guide 13 is inserted through the insertion portion 6, the operation section 7 and the universal cable 8, and is connected to the light source apparatus 3 via the light source connector 9. By the configuration as above, the illuminating light emitted from the light source apparatus 3 is supplied to the illumination lens 12 via the light guide 13, and the object ahead of the insertion portion 6 is illuminated.

Further, at the distal end portion of the insertion portion 6, an objective lens 14 that forms an optical image of the illuminated object is provided adjacently to the illumination lens 12. An image pickup device 15 such as a CCD is provided at an image formation position of the objective lens 14. The image pickup device 15 photoelectrically converts the optical image that is formed and generates an image pickup signal. A signal line 16 is connected to the image pickup device 15. The signal line 16 is connected to the video processor 4 via the electric cable 10 and the electric connector 11. Thereby, the image pickup signal generated by the image pickup device 15 is supplied to the video processor 4 via the signal line 16.

The video processor 4 applies signal processing to the image pickup signal supplied from the image pickup device 15 by a video signal processing circuit not illustrated, and generates a video signal. The video processor 4 outputs the video signal to the monitor 5 to display the video signal on a display screen of the monitor 5.

Next, a detailed configuration of the light source apparatus 3 will be described.

The light source apparatus 3 is configured by having an optical system 21, a filter switching section 22, an LED drive section 23, a control section 24 including a memory 24a, an operation panel 25 and a communication cable 26.

The optical system 21 is configured by having a white color LED 31, a lens 32, a moving motor 33, an optical filter 34, a temperature sensor 35, a voltage detecting section 36, a purple LED 37, a lens 38, a dichroic filter 39, a lens 40, a temperature sensor 41 and a voltage detecting section 42.

The white color LED 31 as a light source having a semiconductor device a light intensity of which deteriorates with a lighting time period emits lights including a first wavelength band in a vicinity of 540 nm for use in narrow band observation and a second wavelength band of 430 nm to 700 nm except for the first wavelength band (in the vicinity of 540 nm). The lens 32 is provided on an optical path of the light which the white color LED 31 emits, and condenses the light emitted from the white color LED 31.

The moving motor 33 moves the optical filter 34 in a perpendicular direction to the optical path of the white color LED 31 and takes the optical filter 34 in and out from the optical path of the white color LED 31, based on control of the filter switching section 22. Taking in and out of the optical filter 34 is performed in accordance with an imaging mode.

The present embodiment has a normal observation mode and a narrow band observation mode as the imaging modes.

When a user operates the operation panel 25, and selects the imaging mode, an imaging mode signal is supplied to the control section 24 from the operation panel 25. Note that the imaging mode may be changed with an operation switch not illustrated provided at the operation section 7 of the endoscope 2, or an operation switch not illustrated provided at the video processor 4 or the like.

The control section 24 supplies a control signal corresponding to the imaging mode signal supplied from the operation panel 25 to the filter switching section 22. When the filter switching section 22 receives the control signal from the control section 24, the filter switching section 22 controls the moving motor 33 to move the optical filter 34 in the perpendicular direction to the optical path of the white color LED 31 so that the optical filter 34 is in a position corresponding to the selected imaging mode.

When the normal observation mode is selected, the filter switching section 22 controls the moving motor 33 so that the optical filter 34 is not inserted into the optical path of the white color LED 31. Further, when the narrow band observation mode is selected, the filter switching section 22 controls the moving motor 33 so that the optical filter 34 is inserted into the optical path of the white color LED 31.

When the optical filter 34 is inserted in the optical path of the white color LED 31, the optical filter 34 transmits a light of the first wavelength band in the vicinity of 540 nm for use in the narrow band observation from the lights including the first and the second wavelength bands of the white color LED 31.

The control section 24 transmits information of the imaging mode and the like to the video processor 4 via the communication cable 26.

Further, the control section 24 outputs lighting current signals and lighting shutoff signals of the white color LED 31 and the purple LED 37 to the LED drive section 23 from the information of the imaging mode, a rotational position, and light adjustment.

The LED drive section 23 performs drive of the white color LED 31 and the purple LED 37 in accordance with the lighting current signals and the lighting shutoff signals supplied from the control section 24. More specifically, the LED drive section 23 lights the white color LED 31 at a time of the normal observation mode, and lights the white color LED 31 and the purple LED 37 at a time of the narrow band observation mode.

The purple LED 37 as a light source having a semiconductor device a light intensity of which deteriorates with a lighting time period emits a light of a third wavelength band in a vicinity of 415 nm that differs from the first and the second wavelength bands. The lens 38 is provided on an optical path of the light emitted by the purple LED 37, and condenses the light emitted from the purple LED 37.

The dichroic filter 39 reflects the light of the wavelength in the vicinity of 415 nm (the third wavelength band) of the purple LED 37, and transmits lights of the wavelength bands other than the third wavelength band. The dichroic filter 39 reflects the light which is emitted from the purple LED 37 and condensed in the lens 38, and combines the optical path of the purple LED 37 with the optical path of the light emitted from the white color LED 31.

The lens 40 condenses the light from the dichroic filter 39, and supplies the light to an incident end face of the light guide 13 which protrudes from the light source connector 9.

Next, deterioration correction processing of the light source apparatus 3 will be described. The deterioration correction processing is executed by the control section 24 of the light source apparatus 3 every time a cumulative lighting time period of the white color LED 31 reaches 3000 hours.

The control section 24 is supplied with a substrate temperature of a substrate on which the white color LED 31 is mounted, from the temperature sensor 35. Further, the control section 24 is provided with a voltage value of the white color LED 31, from the voltage detecting section 36.

The control section 24 calculates a junction temperature of the white color LED 31 by using the substrate temperature of the white color LED 31 from the temperature sensor 35, the voltage value of the white color LED 31 from the voltage detecting section 36, and equation 1 which will be described later.

More specifically, as shown in equation 1, a junction temperature $T_j$ of the white color LED 31 is calculated by a thermal resistance $R_{\theta j\text{-}ref}$ of the substrate on which the white color LED 31 is mounted being multiplied by an input power $P_{Diss}$, and a substrate temperature $T_{ref}$ being added to the multiplied result. Note that the input power $P_{Diss}$ is calculated by a value of a current inputted in the white color LED 31 being multiplied by a voltage value detected by the voltage detecting section 36.

$$\text{Junction temperature } T_j = \text{thermal resistance } R_{\theta j\text{-}ref} \times \text{input power } P_{Diss} + \text{substrate temperature } T_{ref} \quad \text{(equation 1)}$$

Likewise, the control section 24 is supplied with a substrate temperature of a substrate on which the purple LED 37 is mounted, from the temperature sensor 41, and a voltage value of the purple LED 37 from the voltage detecting section 42. The control section 24 calculates a junction temperature of the purple LED 37 by using the substrate temperature of the purple LED 37 from the temperature sensor 41, the voltage value of the purple LED 37 from the voltage detecting section 42, and equation 1 described above.

Subsequently, the control section 24 measures a lighting time period of the white color LED 31 and a lighting time period of the purple LED 37 respectively, and stores the measured lighting time periods in the memory 24a for each of the calculated junction temperature ranges.

FIG. 2 is a diagram for explaining an example of an address map of the memory which stores the lighting time periods of the respective LEDs for each junction temperature range.

As shown in FIG. 2, for example, in a relative address "0," a lighting time period of the white color LED 31 in a range of the junction temperature of 80 to 90° C. is stored, and in a relative address "4," a lighting time period of the white color LED 31 in a range of the junction temperature of 90 to 100° C. is stored. Likewise, in a relative address "1C," a lighting time period of the purple LED 37 in a range of the junction temperature of 80 to 90° C. is stored, and in a relative address "20," a lighting time period of the purple LED 37 in a range of the junction temperature of 90 to 100° C. is stored.

Further, in the memory 24a of the control section 24, a deterioration factor table in which deterioration factors to the respective junction temperature ranges are associated is stored.

FIG. 3 is a diagram for explaining an example of the deterioration factor table.

In the deterioration factor table as a light intensity deterioration characteristic storing section, a deterioration factor of the white color LED 31 and a deterioration factor of the purple LED 37 are associated with each of the junction temperature ranges. For example, the deterioration factors of the white color LED 31 and the purple LED 37 in the range of the junction temperature of 80 to 90° C. are respectively 0.002 (%/time) and 0.00133 (%/time).

The control section 24 calculates the deterioration rates (deteriorated light intensities) of the white color LED 31 and the purple LED 37 respectively, based on the use time periods of the white color LED 31 and the purple LED 37, the calculated junction temperatures, and the deterioration factors as the light intensity deterioration characteristics stored in the deterioration factor table. When the control section 24 calculates the deterioration rates of the white color LED 31 and the purple LED 37, the control section 24 stores the use time periods of the white color LED 31 and the purple LED 37 for each junction temperature range, and calculates the deterioration rates of the white color LED 31 and the purple LED 37 when a total use time period of the white color LED 31 reaches 3000 hours. Note that the control section 24 may calculate the deterioration rates of the white color LED 31 and the purple LED 37 every time the control section 24 counts the use time periods of the white color LED 31 and the purple LED 37 for each junction temperature range, and may update and store the calculated deterioration rates in the memory 24a.

FIG. 4 is a diagram for explaining a calculation example of the deterioration rates.

The calculation example of the deterioration rates of FIG. 4 shows the deterioration rates of the white color LED 31 and the purple LED 37 at a time of the total use time period of the white color LED 31 reaching 3000 hours.

In the example of FIG. 4, the white color LED 31 is used for 500 hours in the range of the junction temperature of 90 to 100° C., is used for 2000 hours in the range of the junction temperature of 100 to 110° C., and is used for 500 hours in the range of the junction temperature of 110 to 120° C. Further, the purple LED 37 is used for 200 hours in the range of the junction temperature of 90 to 100° C., is used for 500 hours in the range of the junction temperature of 100 to 110° C., and is used for 300 hours in the range of the junction temperature of 110 to 120° C.

For example, the deterioration rate of the white color LED 31 in the range of the junction temperature of 90 to 100° C. is calculated as 1.5% by 0.003 of the deterioration factor of the white color LED 31 in the range of the junction temperature of 90 to 100° C. of FIG. 3 being multiplied by 500 of the use time period. Likewise, the deterioration rate of the white color LED 31 in the range of the junction temperature of 100 to 110° C. is calculated as 8.34%, and the deterioration rate of the white color LED 31 in the range of the junction temperature of 110 to 120° C. is calculated as 2.75%. The deterioration rates calculated as above are all added, whereby the deterioration rate of the white color LED 31 at a time of use of 3000 hours is calculated as 12.59%. Likewise, the deterioration rate of the purple LED 37 at a time of use of 1000 hours is calculated as 2.58%.

FIG. 5 is diagrams for explaining current-light intensity characteristics of currents that drive the respective LEDs and light intensities.

Figure 5A:
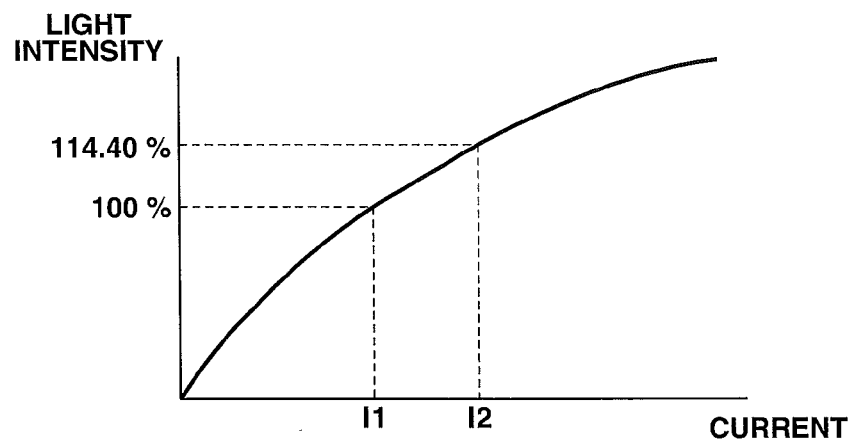
FIG. 5A is a diagram showing current-light intensity characteristics of a current that drives a white color LED 31 and a light intensity.
Figure 5B:
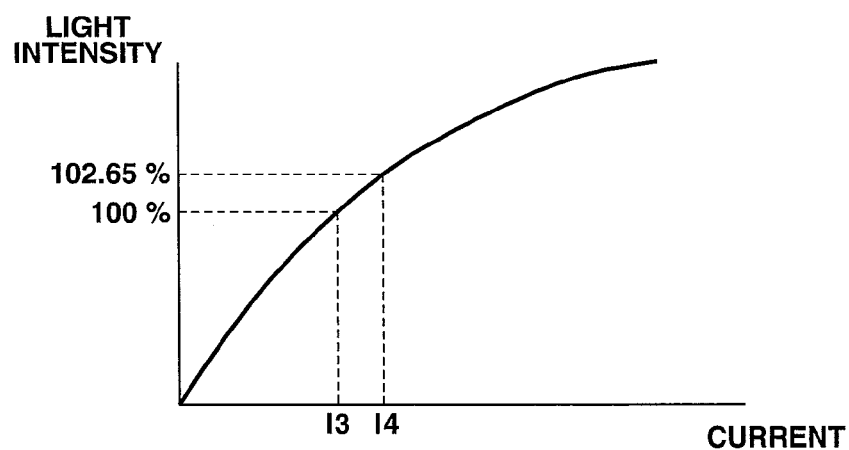
FIG. 5B is a diagram showing current-light intensity characteristics of a current that drives a purple LED 37 and a light intensity.

FIG. 5A shows current-light intensity characteristics of a current that drives the white color LED 31 and a light intensity, and FIG. 5B shows current-light intensity characteristics of a current that drives the purple LED 37 and a light intensity. The current-light intensity characteristics as the light source drive characteristic storing section shown in FIG. 5A and FIG. 5B are stored in the memory 24a of the control section 24. As shown in FIG. 5A, a current I1 is applied to the white color LED 31 as an initial value so that the light intensity is 100%. Likewise, a current I3 is applied to the purple LED 37 as an initial value so that the light intensity is 100%.

The control section 24 controls the currents that drive the white color LED 31 and the purple LED 37, based on the deterioration rates calculated as described above, and the current-light intensity characteristics shown in FIG. 5A and FIG. 5B.

More specifically, the control section 24 calculates an increasing amount of the light intensity at a time of correction processing by an inverse number of (100%–deterioration rate). When the deterioration rate of the white color LED 31 is calculated as 12.59% as described above, the control section 24 performs control of changing the current that drives the white color LED 31 to a current I2 from the current I1 so that the light intensity of the white color LED 31 becomes 114.40% (inverse number of (100%–12.59%)). Namely, the control section 24 outputs a lighting current signal for changing the current that drives the white color LED 31 from the current I1 to the current I2 to the LED drive section 23. Thereby, the light with the light intensity of 100% is emitted from the white color LED 31 because the deterioration rate of the white color LED 31 is 12.59%.

Likewise, the control section 24 performs control to change the current that drives the purple LED 37 from the current I3 to a current I4 so that the light intensity of the purple LED 37 becomes 102.65% (inverse number of (100%–2.58%)). Thereby, the light with the light intensity of 100% is emitted from the purple LED 37 because the deterioration rate of the purple LED 37 is 2.58%.

As above, the control section 24 performs deterioration correction processing of correcting the light intensities of the white color LED 31 and the purple LED 37 to 100% every time the total use time period of the white color LED 31 reaches 3000 hours.

Next, an operation of the light source apparatus 3 that is configured as above will be described.

Figure 6:
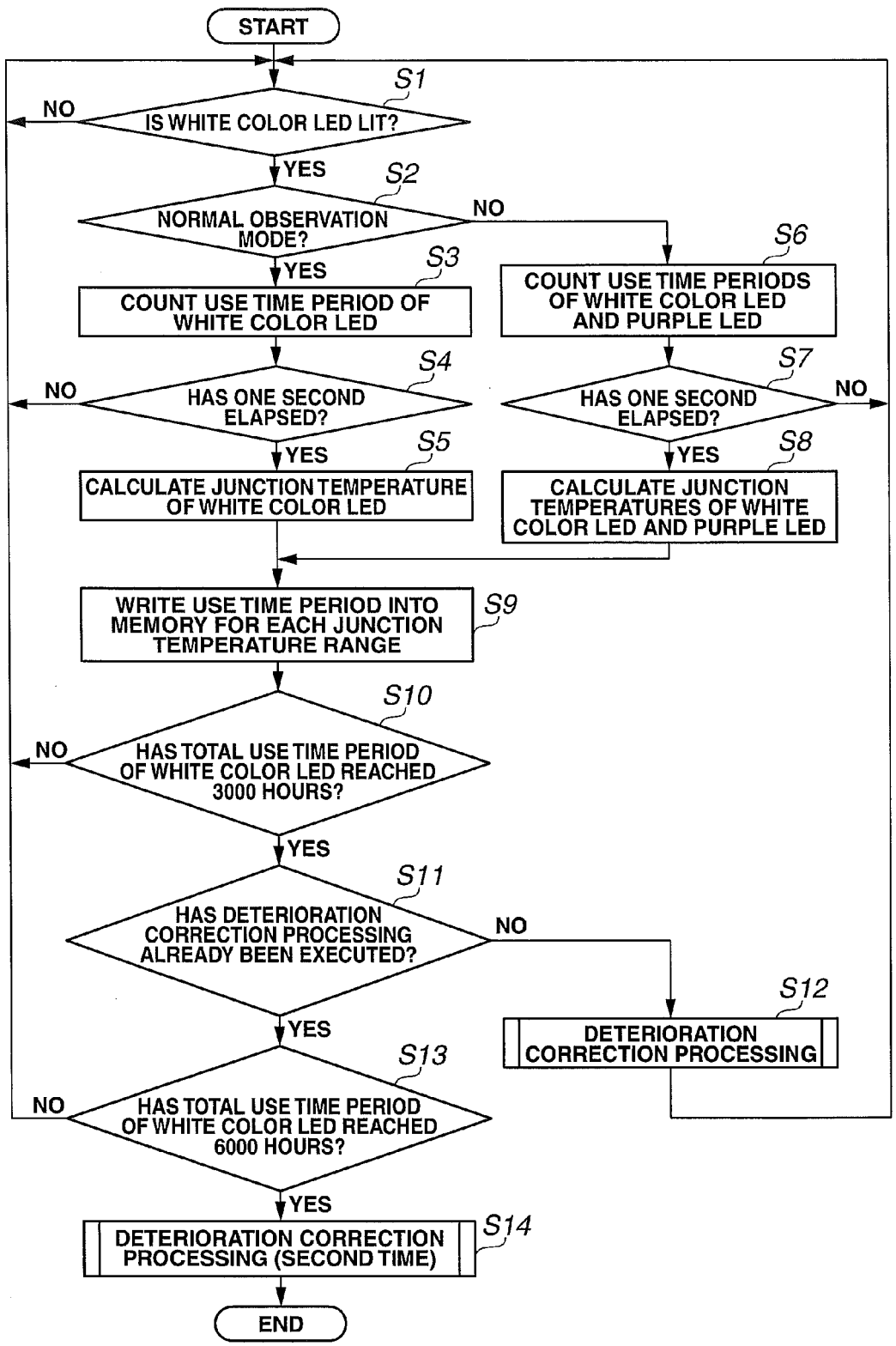
FIG. 6 is a flowchart showing an example of a flow of processing of correcting deterioration of a light source of a light source apparatus 3.

FIG. 6 is a flowchart showing an example of a flow of processing of correcting deterioration of the light source of the light source apparatus 3. The processing of FIG. 6 is executed by the control section 24.

First, it is determined whether or not the white color LED 31 is lit (step S1). In the present embodiment, the white color LED 31 is lit in both of the normal observation mode and the narrow band observation mode, and therefore, in the processing of step S1, whether the white color LED 31 is lit or not can be determined. When it is determined that the white color LED 31 is not lit, the result is NO, and the flow returns to step S1, where the same processing is repeated. In contrast with this, when it is determined that the white color LED 31 is lit, the result is YES, and it is determined whether or not the imaging mode is a normal observation mode (step S2).

When the imaging mode is determined as a normal observation mode, the result is YES, the use time period of the white color LED 31 is counted (step S3), and it is determined whether or not one second elapses (step S4). When it is determined that one second does not elapse, the result is NO, and the flow returns to step S1, where the same processing is repeated. When it is determined that one second elapses, the junction temperature of the white color LED 31 is calculated (step S5).

When it is determined that the imaging mode is not a normal observation mode, that is, the imaging mode is determined as a narrow band observation mode in step S2, the result is NO, the use time periods of the white color LED 31 and the purple LED 37 are counted (step S6), and it is determined whether or not one second elapses (step S7). When it is determined that one second does not elapse, the result is NO, and the flow returns to step S1, where the same processing is repeated. When it is determined that one second elapses, the junction temperatures of the white color LED 31 and the purple LED 37 are calculated (step S8). Steps S3 and S4, and steps S6 and S7 configure a lighting time period measuring section that measures the lighting time periods of the white color LED 31 and the purple LED 37. Further, step S5 and step S8 configure a junction temperature calculating section that calculates the junction temperatures of the white color LED 31 and the purple LED 37.

When the processing of step S5 or step S8 is executed, the use time periods are written in the memory 24a for each junction temperature range (step S9), and it is determined whether or not the total use time period of the white color LED 31 reaches 3000 hours (step S10). When it is determined that the total use time period of the white color LED 31 does not reach 3000 hours, the result is NO, the flow returns to step S1, where the same processing is repeated. Contrary to the above, when it is determined that the total use time period of the white color LED 31 reaches 3000 hours, the result is YES, and it is determined whether or not the deterioration correction processing is already executed (step S11). When it is determined that the deterioration correction processing is not executed yet, the result is NO, the deterioration correction processing is executed (step S11), and the flow returns to step S1, where the same processing is repeated.

When it is determined that the deterioration correction processing is already executed, the result is YES, and it is determined whether or not the total use time period of the white color LED 31 reaches 6000 hours (step S13). When it is determined that the total use time period of the white color LED 31 does not reach 6000 hours, the result is NO, and the flow returns to step S1, where the same processing is repeated. When it is determined that the total use time period of the white color LED 31 reaches 6000 hours, the result is YES, the deterioration correction processing (the second time) is executed (step S14), and the processing is ended.

The deterioration correction processing of step S12 and the deterioration correction processing of step S14 (the second time) configure a deteriorated light intensity calculating section that calculates the deterioration rates (deterioration light intensities) respectively based on the use time periods for each junction temperature range and the light intensity deterioration characteristics of FIG. 3 of the white color LED 31 and the purple LED 37 as described above, and a light source power control section that controls (corrects) the currents that drive the white color LED 31 and the purple LED 37 respectively based on the calculated deterioration rates, and the current-light intensity characteristics of FIG. 5.

As above, the light source apparatus 3 calculates the deterioration rates of the white color LED 31 and the purple LED 37 based on the use time periods of the white color LED 31 and the purple LED 37 which are measured for each junction temperature range, and the deterioration factors of the white color LED 31 and the purple LED 37. Subsequently, the light source apparatus 3 controls the currents that drive the white color LED 31 and the purple LED 37 respectively based on the calculated deterioration rates of the white color LED 31 and the purple LED 37, and the current-light intensity characteristics of the white color LED 31 and the purple LED 37. As a result, the currents that drive the white color LED 31 and the purple LED 37 can be respectively corrected in accordance with the accurate deterioration rates calculated for each junction temperature range.

Consequently, according to the light source apparatus of the present embodiment, the light intensities of the LEDs can be accurately corrected.

(Modification)

Figure 8:
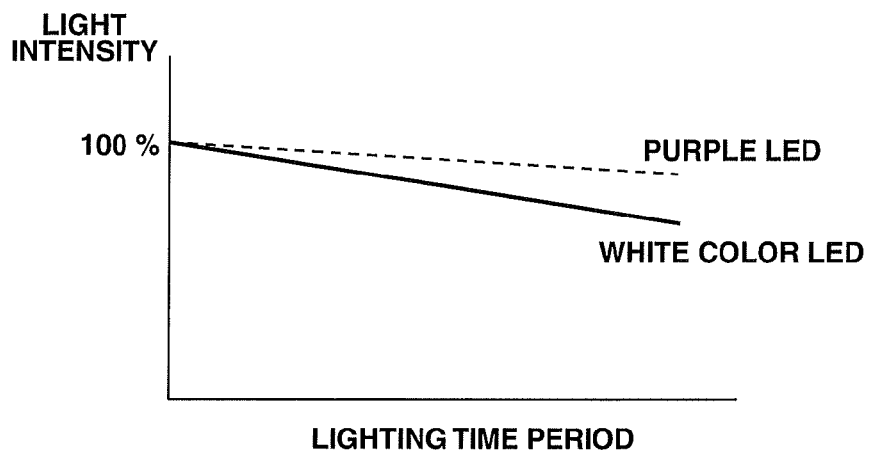
FIG. 8 is a diagram showing light intensity deterioration characteristics of a white color LED and a purple LED.

In the light source apparatus 3 including a plurality of colors, in this case, the white color LED 31 and the purple LED 37, the deterioration rates differ between the white color LED 31 and the purple LED 37 according to the junction temperature range and the like. Therefore, as shown in FIG. 8, even with the same lighting time period, the deterioration characteristics of the light intensity of the white color LED 31 and the light intensity of the purple LED 37 differ from each other. Further, the light source apparatus 3 lights only the white color LED 31 at the time of the normal observation mode, and lights the white color LED 31 and the purple LED 37 at the time of the narrow band observation mode. As above, in the light source apparatus 3, the lighting time periods of the white color LED 31 and the purple LED 37 differ in accordance with the imaging mode. Therefore, if the light source apparatus 3 is used for a long time period, a color balance of the white color LED 31 and the purple LED 37 cannot be kept constant.

When a difference of the deterioration rates of the white color LED 31 and the purple LED 37 becomes 5% or more, the light source apparatus 3 of the present modification executes deterioration correction processing for keeping the color balance constant. In the deterioration correction processing for keeping the color balance constant, the control section 24 of the light source apparatus 3 corrects the deterioration rate of the white color LED 31 to match the deterioration rate of the white color LED 31 with the deterioration rate of the purple LED 37. In the deterioration correction processing of the present modification, the deterioration rates (deterioration light intensities) of the white color LED 31 and the purple LED 37 are respectively calculated, and based on the calculated deterioration rates, and the deteriorated light intensity characteristics of FIG. 5, processing of correcting the current that drives the white color LED 31 is executed so that the deterioration rate of the white color LED 31 and the deterioration rate of the purple LED 37 become the same.

For example, when the deterioration rate of the white color LED 31 when the white color LED 31 is used for 3000 hours is 10%, and the deterioration rate of the purple LED 37 is 3%, the current that drives the white color LED 31 is corrected so that the deterioration rate of the white color LED 31 becomes 3%. Note that in the deterioration correction processing, the deterioration rate of the white color LED 31 is corrected to correspond to the deterioration rate of the purple LED 37, but the deterioration rate of the purple LED 37 may be corrected to correspond to the deterioration rate of the white color LED 31.

Figure 7:
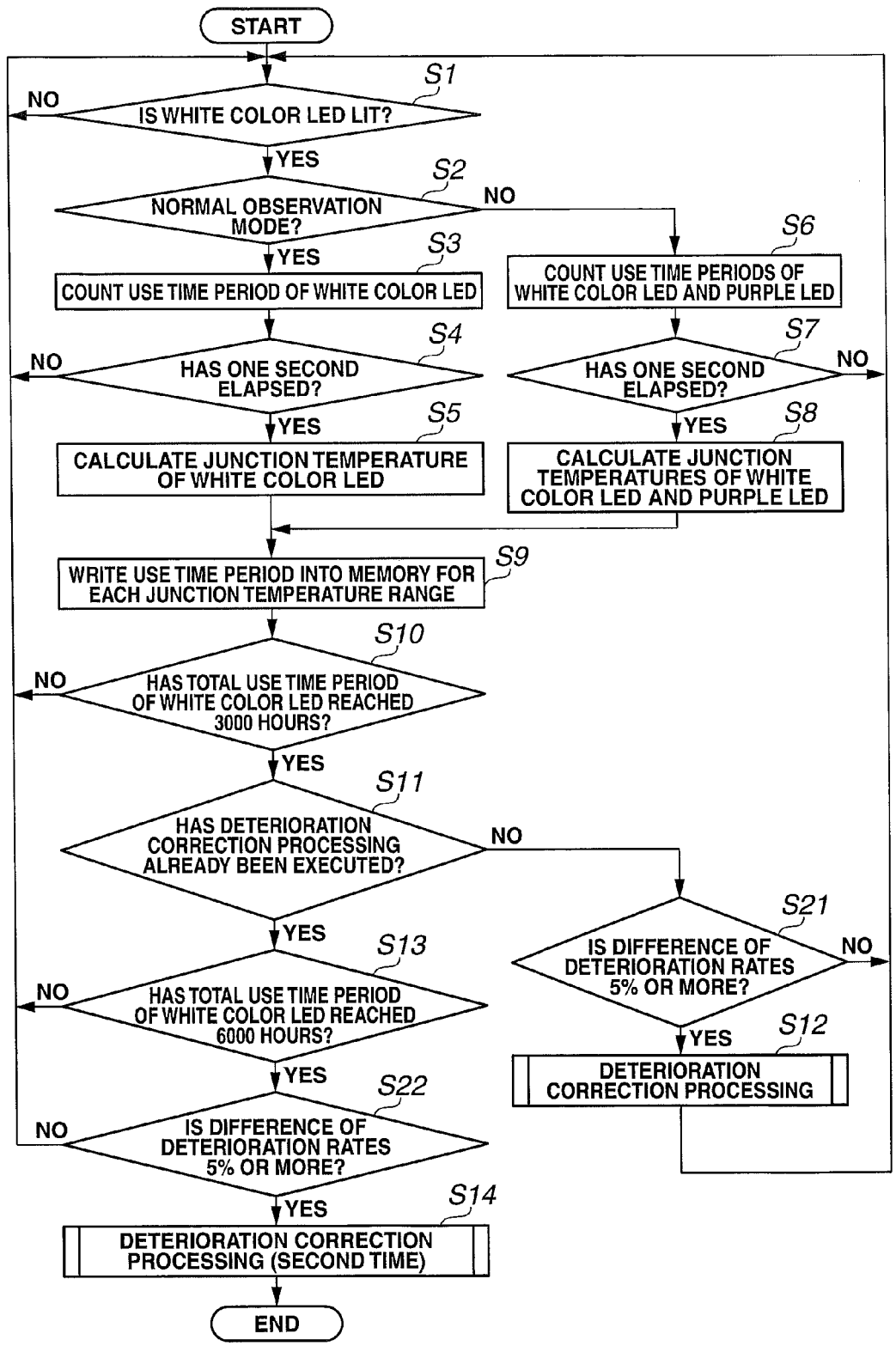
FIG. 7 is a flowchart showing an example of a flow of processing of correcting a color balance of the light source apparatus 3.

FIG. 7 is a flowchart showing an example of a flow of processing of correcting the color balance of the light source apparatus 3. Note that in FIG. 6, the same processing as that in FIG. 7 is assigned with the same reference sign, and the description thereof will be omitted.

When it is determined that the deterioration correction processing is not executed yet in step S11, it is determined whether or not the difference of the deterioration rates of the white color LED 31 and the purple LED 37 is 5% or more (step S21). When it is determined that the difference of the deterioration rates of the white color LED 31 and the purple LED 37 is not 5% or more, the result is NO, and the flow returns to step S1, where the same processing is repeated. When it is determined that the difference of the deterioration rates of the white color LED 31 and the purple LED 37 is 5% or more, the result is YES, the deterioration correction processing is executed in step S12, and the processing returns to step S1.

Further, when it is determined that the deterioration correction processing is already executed, in step S11, and it is determined that the total use time period of the white color LED 31 reaches 6000 hours in step S13, it is determined whether or not the difference of the deterioration rates of the white color LED 31 and the purple LED 37 is 5% or more (step S22). When it is determined that the difference of the deterioration rates of the white color LED 31 and the purple LED 37 is not 5% or more, the result is NO, and the flow returns to step S1, where the same processing is repeated. When it is determined that the difference of the deterioration rates of the white color LED 31 and the purple LED 37 is 5% or more, the result is YES, the deterioration correction processing (the second time) is executed in step S14, and the processing returns to step S1.

Note that in the deterioration correction processing of step S12 and the deterioration correction processing (the second time) of step S14, as described above, the deterioration rates (deterioration light intensities) of the white color LED 31 and the purple LED 37 are respectively calculated, and based on the calculated deterioration rates and the current-light intensity characteristics of FIG. 5, processing of correcting the current that drives the white color LED 31 or the purple LED 37 to achieve the same deterioration rate as the deterioration rate of any one of the LEDs is executed.

Conventionally, when the color balance of the light source apparatus including LEDs of a plurality of colors is kept, the emitted light is fed back and the light intensity of the return light which is fed back is detected with a light sensor. Subsequently, based on the light intensity detected by the light sensor, the currents that drive the respective LEDs of a plurality of colors are controlled, and the color balance is kept. In such a conventional light source apparatus, an optical sensor in the light source apparatus needs to be provided, and the cost is increased.

In contrast with the above, the light source apparatus 3 of the modification corrects the current that drives the white color LED 31 or the purple LED 37 to achieve the same deterioration rate as the deterioration rate of any one of the LEDs, based on the calculated deterioration rates, and the deteriorated light intensity characteristics of FIG. 5. As a result, the light source apparatus 3 of the modification can keep the color balance favorable without providing an optical sensor, and therefore, can reduce the cost.

Note that as for the respective steps in the flowcharts in the present description, the execution sequence thereof may be changed, a plurality of the steps may be simultaneously executed, or the respective steps may be executed in different sequence each time the respective steps are executed, as long as it does not contradict the properties thereof.

The present invention is not limited to the embodiments described above, and various modifications, alterations and the like can be made within the range without departing from the gist of the present invention.

What is claimed is:

1. A light source apparatus configured by a light source having a semiconductor device, a light intensity of which deteriorates with a lighting time period, comprising:
   a lighting time period measuring section that measures a lighting time period of the light source;
   a junction temperature calculating section that calculates a junction temperature of the light source;
   a light intensity deterioration characteristic storing section that stores a light intensity deterioration characteristic based on the junction temperature of the light source;
   a light source drive characteristic storing section that stores characteristics of power that drives the light source and a light intensity;
   a deteriorated light intensity calculating section that, every time a total use time period of the light source reaches a predetermined total use time period, calculates a deteriorated light intensity based on the lighting time period measured by the lighting time period measuring section, the junction temperature calculated by the junction temperature calculating section, and the light intensity deterioration characteristic stored in the light intensity deterioration characteristic storing section; and a light source power control section that controls power that drives the light source, based on the deteriorated light intensity calculated by the deteriorated light intensity calculating section, and the characteristics stored in the light source drive characteristic storing section.

2. The light source apparatus according to claim 1, wherein the light source apparatus is configured by a plurality of light sources, the lighting time period measuring section measures respective lighting time periods of the plurality of light sources, the junction temperature calculating section calculates respective junction temperatures of the plurality of light sources, the light intensity deterioration characteristic storing section stores light intensity deterioration characteristics based on the respective junction temperatures of the plurality of light sources, the light source drive characteristic storing section stores characteristics of power that drives the respective plurality of light sources and light intensities, the deteriorated light intensity calculating section calculates respective deteriorated light intensities of the plurality of light sources, based on the respective lighting time periods of the plurality of light sources measured by the lighting time period measuring section, the respective junction temperatures of the plurality of light sources calculated by the junction temperature calculating section, and the respective light intensity deterioration characteristics of the plurality of light sources stored in the light intensity deterioration characteristic storing section, and the light source power control section controls power that drives the plurality of light sources to keep a color balance of the plurality of light sources constant, based on the respective deteriorated light intensities of the plurality of light sources calculated by the deteriorated light intensity calculating section, and the respective characteristics of the plurality of light sources stored in the light source drive characteristic storing section.

* * * * *